United States Patent [19]

Lokkesmoe et al.

[11] Patent Number: 5,409,713

[45] Date of Patent: Apr. 25, 1995

[54] PROCESS FOR INHIBITION OF MICROBIAL GROWTH IN AQUEOUS TRANSPORT STREAMS

[75] Inventors: Keith Lokkesmoe, Burnsville; Keith Olson, Apple Valley, both of Minn.

[73] Assignee: Ecolab Inc., St. Paul, Minn.

[21] Appl. No.: 32,624

[22] Filed: Mar. 17, 1993

[51] Int. Cl.⁶ .................. A01N 59/00; A01N 37/16; C02F 1/50; C02F 1/72
[52] U.S. Cl. .................. 424/616; 514/557; 422/28; 422/29; 210/759; 426/331; 426/333; 426/335; 426/532
[58] Field of Search .............. 514/557; 424/616; 422/28, 29; 426/331, 333, 335, 532; 210/759

[56] References Cited

U.S. PATENT DOCUMENTS

| | | | |
|---|---|---|---|
| 2,466,663 | 4/1949 | Russ et al. | 167/58 |
| 2,512,640 | 6/1950 | Greenspan et al. | 514/557 |
| 2,668,150 | 2/1954 | Luvisi | 252/321 |
| 3,042,621 | 7/1962 | Kirschenbauer | 252/99 |
| 3,150,096 | 9/1964 | Schmidt et al. | 252/106 |
| 3,218,260 | 11/1965 | Lewandowski | 252/142 |
| 3,297,456 | 1/1967 | Newell | 106/3 |
| 3,438,906 | 4/1969 | Duvall | 252/106 |
| 3,525,696 | 8/1970 | Schmidt et al. | 252/106 |
| 3,560,390 | 2/1971 | Gaines | 252/107 |
| 3,650,965 | 3/1972 | Cantor et al. | 252/106 |
| 3,867,300 | 2/1975 | Karabinos | 252/106 |
| 3,915,633 | 10/1975 | Ramachanoran | 252/95 |
| 4,002,775 | 1/1977 | Kabara | 426/532 |
| 4,051,058 | 9/1977 | Bowing et al. | 252/186 |
| 4,051,059 | 9/1977 | Bowing et al. | 252/186 |
| 4,164,477 | 8/1979 | Whitley | 252/106 |
| 4,203,765 | 5/1980 | Claeys et al. | 252/186 |
| 4,376,787 | 3/1983 | Lentsch et al. | 424/315 |
| 4,404,040 | 9/1983 | Wang | 252/106 |
| 4,406,884 | 9/1983 | Fawzi et al. | 424/81 |
| 4,410,442 | 10/1983 | Lucas et al. | 252/107 |
| 4,430,381 | 2/1984 | Harvey et al. | 428/284 |
| 4,534,945 | 8/1985 | Hopkins et al. | 423/273 |
| 4,557,935 | 12/1985 | af Ekenstam et al. | 514/928 |
| 4,647,458 | 3/1987 | Ueno et al. | 422/28 |
| 4,715,980 | 12/1987 | Lopes et al. | 252/106 |
| 4,776,974 | 10/1988 | Stanton et al. | 252/106 |
| 4,900,721 | 2/1990 | Bansemir et al. | 514/714 |
| 4,920,100 | 4/1990 | Lehmann et al. | 514/635 |
| 4,945,110 | 7/1990 | Brokken et al. | 514/517 |
| 5,013,560 | 5/1991 | Stentz et al. | 424/653 |
| 5,017,617 | 5/1991 | Kihara et al. | 514/635 |
| 5,122,538 | 6/1992 | Lokkesmoe et al. | 514/557 |
| 5,139,788 | 8/1992 | Schmidt | 424/616 |
| 5,200,189 | 4/1993 | Oakes et al. | 514/558 |

FOREIGN PATENT DOCUMENTS

| | | |
|---|---|---|
| 553057 | 2/1959 | Canada . |
| 657564 | 2/1963 | Canada . |
| 1018854 | 10/1977 | Canada . |
| 1174976 | 9/1984 | Canada . |
| 0021504 | 1/1981 | European Pat. Off. . |
| 0068552 | 1/1983 | European Pat. Off. . |
| 0083820 | 7/1983 | European Pat. Off. . |
| 0097995 | 1/1984 | European Pat. Off. . |
| 0147102 | 7/1985 | European Pat. Off. . |
| 0218441 | 4/1987 | European Pat. Off. . |
| 244144 | 11/1987 | European Pat. Off. . |

(List continued on next page.)

OTHER PUBLICATIONS

Journal of Food Protection "Food-Grade Chemicals for Use in Designing Food Preservative for Use in Designing Food Preservative Systems", Jon. J. Kabara, vol. 44, Aug. 1981, pp. 633–647.

(List continued on next page.)

Primary Examiner—Allen J. Robinson
Assistant Examiner—John D. Pak
Attorney, Agent, or Firm—Merchant, Gould, Smith, Edell, Welter & Schmidt

[57] ABSTRACT

The invention is a process for preventing microbial growth in aqueous streams by applying peracetic acid to the aqueous stream. Generally, the process of the invention is applicable to aqueous streams used in any number of applications such as the application of streams for the transport of fruits or vegetables into the processing environment and through the various steps of processing.

14 Claims, 5 Drawing Sheets

FOREIGN PATENT DOCUMENTS

| | | |
|---|---|---|
| 0245928 | 11/1987 | European Pat. Off. . |
| 288689 | 11/1988 | European Pat. Off. . |
| 0361955 | 4/1990 | European Pat. Off. . |
| 0375827 | 7/1990 | European Pat. Off. . |
| 2122284 | 9/1972 | France . |
| 2223049 | 10/1974 | France . |
| 59-157007 | 9/1984 | Japan . |
| 62-048612 | 3/1987 | Japan . |
| 1595431 | 9/1990 | Russian Federation . |
| 1135643 | 3/1965 | United Kingdom . |
| 2076286A | 12/1981 | United Kingdom . |
| 2103089A | 2/1983 | United Kingdom . |
| 2187097A | 9/1987 | United Kingdom . |
| 2189394A | 10/1987 | United Kingdom . |
| 2211093 | 6/1989 | United Kingdom . |
| 2257630 | 1/1993 | United Kingdom . |
| WO83/00163 | 1/1983 | WIPO . |
| WO87/03779 | 7/1987 | WIPO . |
| WO87/06470 | 11/1987 | WIPO . |
| 9105842 | 5/1991 | WIPO . |
| WO92/21238 | 12/1992 | WIPO . |
| WO92/21239 | 12/1992 | WIPO . |

OTHER PUBLICATIONS

Keeney, E. L., Sodium Caprylate, *A New and Effective Treatment of Moniliasis of the Skin,* 78 Bull. Johns. Hopkins U. (1946) pp. 333–339.

Morrison, Rbt. T. et al., *Organic Chemistry,* (1959), pp. 438–439.

Canas-Rodriquez A. et al., *The Indentification of the Antimicrobial Factors of the Stomach Contents of Sucking Rabbits,* 100 Biochem. J. (1966) pp. 79–82.

Fay, J. P. et al., *The Inhibitory Action of Fatty Acids on the Growth of Ester–Chia Coli,* 91 J. General Microbiology, (1975) pp. 233–240.

Mulder et al., "Research Note: Salmonella Decontamination of Broiler Carcasses (Chickens) with Lactic Acid L-Cysteine and Hydrogen Peroxide" *Poultry Science,* pp. 1555–1557 (1987).

Kirk–Othmer Encyclopedia of Chemical Technology, Third Edition: (1979) Dicarboxylic Acids, vol. 7, pp. 614–628; Carbonated Beverages (1978) vol. 4, pp. 712–713; Citric Acid, vol. 6, 1979 pp. 159–179, Hydroxy Carboxylic Acids, 1981 vol. 13, pp. 80–121; and Carboxylic Acids, vol. 4, pp. 814–871 (1978).

Committee of Specifications, . . . *Food Chemicals Codex,* 2nd Edition, pp. 12–14 (1972).

*Code of Federal Regulations, Food and Drugs,* Revises as of Apr. 1, 1991, pp. 311–318.

Kirk–Othmer, *Encyclopedia of Chemical Technology,* Third Edition, vol. 12, "Gravity Concentration to Hydrogen Energy", pp. 46–62 (1980).

Dychdala, *Disinfection, Sterilization and Preservation,* Second Edition, "Acid–Anionic Surfactant Sanitizers", pp. 319–324 (1977).

Foegeding et al., *Disinfection, Sterilization and Preservation,* Fourth Edition, "Chemical Food Preservatives", pp. 802–832 (1991).

Stewart et al., *Food Science and Technology,* "A Series of Monographs", pp. 186–187 (1965).

Towle et al., *Industrial Gums Polysaccharides and Their Derivatives,* Second Ed., Chpt. XIX, Pectin, pp. 429–455 (1973).

Gosselin et.al., *Clinical Toxicology of Commercial Products,* Fifth Editon, Section III, Ethylene Glycol, p. 172 (1984).

Chemical Abstracts, Abstract No. 95735r, vol. 111, No. 11 (Sep. 11, 1989).

Seymour A. Block, Disinfection, Sterilization and Preservation, Fourth Edition, 1991, Chpt. 47, "Chemical Food Preservatives".

Seymour A. Block, Disinfection, Sterilization and Preservation, 2nd Edition, 1977, Chpt. 16, "Acid–Anionic Surfactant Sanitizers".

Code of Federal Regulation, 21 C.F.R. Chapter 1, (Apr. 1, 1991 Ed.), pp. 311–318.

The Food Chemical News Guide, Oct. 7, 1991.

The Food Chemical News Guide, Jun. 26, 1989.

Clinical Toxicity of Commerical Products, Fifth Edition, 1984.

S. S. Block, Disinfection, Sterilization and Preservation, 1991, Lea & Febiger, Philadelphia, Chapter 9, p. 179, column 1, lines 13 and 14, see also pp. 167–180.

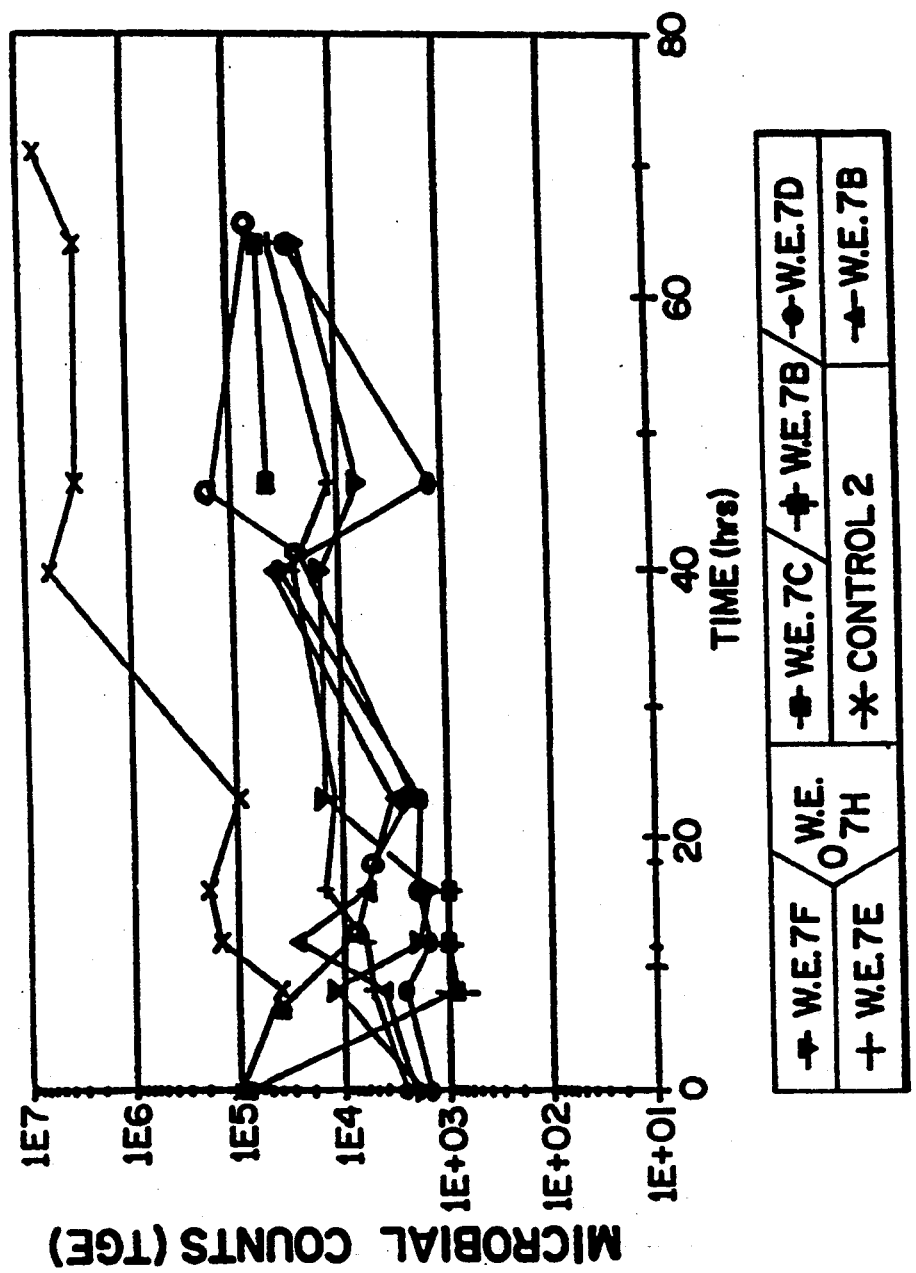

PROCESS FOR INHIBITION OF MICROBIAL GROWTH IN AQUEOUS TRANSPORT STREAMS

FIELD OF THE INVENTION

The invention relates to the control of microbial growth in aqueous streams. More specifically, the invention relates to the control of microbial growth in aqueous streams used for transporting food products in processing environments such as fruit, vegetable and food products, for example, mushrooms, poultry, tomatoes, and the like.

BACKGROUND OF THE INVENTION

The advent of food processing has long since revolutionized both the availability of foods as well as the expectation of consumers for a large variety of high quality food products. Initially, food processing techniques included canning, and later, refrigeration, freezing, freeze drying as well as vacuum packaging. The application of various constituent-based and process-based preservation systems have all lead to a wider availability of high quality food stuffs.

In turn, food pricing and availability is generally subject to various constraints including environmental hazards as well as natural weather cycles, selection and processing considerations, and overall economic and marketing constraints. Given the large volume of food selected and processed on an annual basis, as well as the relative uncontrollability of factors such as the environment and the marketplace, producers strive to economize in the selection and processing of food stuffs. One means of processing a large volume of foods, such as, for example, fruits and vegetables, is after selection, to transport these various food stuffs by an aqueous medium to deliver the food stuffs through various processing steps and environments.

For example, in specific applications, fresh fruits and vegetables may be transported through water streams by food handling equipment used at the processing plant. After picking, fruits and vegetables are introduced into a flume system wherein water acts as a transport medium and a cleaning medium. Water may be used to support and transport the fruits or vegetables from an unloading sight to a final storage or packing or processing location. During the transport, water can take a food item from an initial location through a series of somewhat separate stages to a final station where the produce is removed from the water and packed. The water within each stage may have a varying degree of organic load in the form of any number of sediments and soluble materials. This water is generally recycled.

Given the nature of the food transported as well as the presence of sediments and soluble materials, the water, flume, and other transport or processing equipment may be subject to the growth of unwanted microorganisms. These microorganisms are generally undesirable to the transported food, the water, the flume and may cause buildup on all water contact surfaces of slime or biofilm, which requires frequent cleaning to remove. Further, because the process water and equipment are in contact with food products, the control of unwanted microorganisms presents certain problems created by a food contact environment containing microorganisms.

Ideally, an antimicrobial agent or compound used in such a system will have several important properties in addition to its antimicrobial efficacy. The compound or agent should have no residual antimicrobial activity on the food. Residual activity implies the presence of a film of antimicrobial material which will continue to have antimicrobial effect which may require further rinsing of the food product. The antimicrobial agent preferably should also be odor free to prevent transfer of undesirable odors onto food stuffs. The antimicrobial agent should also be composed of direct food additive materials which will not effect food if contamination occurs, nor effect humans should incidental ingestion result. In addition, the antimicrobial agent should preferably be composed of naturally occurring or innocuous ingredients, which are chemically compatible with the environment and cause no concerns for toxic residues within the flume water.

The use of other antimicrobial agents in the control of microorganisms is well known for various applications. For example, Grosse Böwing et al U.S. Pat. Nos. 4,051,058 and 4,051,059 used peracetic acid as a food grade sanitizer in a variety of applications. Further, Greenspan et al, U.S. Pat. No. 2,512,640 teach the use of a peracetic acid composition comprising 500 ppm or more of peracetic acid for the treatment of various fruit and vegetable compositions in a spray applicator. Greenspan et al, Food Technology, Vol. 5, No. 3, 1951, similarly discloses spray compositions which may be applied to fresh fruits and vegetables comprising peracetic acid. Langford, UK Patent Application GB 2 187 958 A discloses the use of peracetic acid and propionic acid for the treatment of fungi in microbial plant pathogens on growing plants and especially edible crops.

In other publications, Baldry et al, "Disinfection of Sewage Effluent with Peracetic Acid", Wat. Sci. Tech., Vol. 21, No. 3, pp. 203–206, 1989; and Poffé et al, "Disinfection of Effluents from Municipal Sewage Treatment Plants with Peroxy Acids", Zbl. Bakt. Hyg. I. Abt. Orig. B 167, 337–346 (1978) both disclose the use of peroxy acids for the treatment of effluents streams and municipal sewage applications. Hutchings et al, "Comparative Evaluation of the Bactericidal Efficiency of Peracetic Acid, Quaternaries, and Chlorine-Containing Compounds", Society of American Bacteriologists, Abstracts of Papers Presented at the 49th General Meeting, discloses-the generally efficacy of peracetic acid compared to various other antimicrobial compounds.

Additionally, Branner-Jorgensen et al, U.S. Pat. No. 4,591,565 discloses the reduction of the thermal stability of rennet through the use of aqueous-based aliphatic or inorganic peroxy acids. Block, "Disinfection, Sterilization, and Preservation", Fourth Edition, Chapter 9, pages 167–181, discloses the various characteristics and attributes of peroxygen compounds. However, generally the art has taught against the use of percarboxylic acids in aqueous streams due to concerns of compound stability in the presence of high concentrations of organic matter.

In the past, flume apparatus have generally been treated with sodium hypochlorite and chlorine dioxide. Generally, these materials are effective in preventing the unwanted growth of microorganisms. However, the use rate of these chlorine-based antimicrobials is very high because they tend to be rapidly consumed by the high organic load included in both the fruits or vegetables and soil. Further, upon consumption, compounds such as chlorine dioxide decompose producing by-products such as chlorites and chlorates, while hypochlorite produces trichloromethanes which may be toxic in very low concentrations. Lastly, chlorine dioxide is a toxic gas with an acceptable air concentration limit of 0.1 ppm. Exposure to $ClO_2$ often leads to headaches, nausea, and respiratory problems, requiring expensive and intricate safety devices and equipment when it is used.

Iodophor antimicrobial agents have also been used for various antimicrobial applications. However, iodophor compounds tend to decompose or may be lost by evaporation when used in an aqueous medium. Thus, long term activity requires a high iodophor concentration.

As a result, a need exists in the food processing industry to provide a means of food transport which also controls soil and microbial load without the use of high concentrations of antimicrobials such as chlorinated compounds and other halogenated constituents.

SUMMARY OF THE INVENTION

The invention is a process for preventing microbial growth in aqueous streams comprising the step of applying a percarboxylic acid or a mixture of percarboxylic acids to the aqueous stream.

The process of the invention is unexpectedly effective in preventing the growth of unwanted microorganisms in food transport apparatus. The consumption of peracetic acid is unexpectedly low in view of the organic loading of both fruits or vegetables and microbial soils within the flume water.

The process of the invention provides an antimicrobial agent useful in process water for transporting food products which has a high degree of antimicrobial efficacy and which is safely ingestible by humans while imposing no environmental incompatibility.

Differentiation of antimicrobial "-cidal" or "-static" activity, the definitions which describe the degree of efficacy, and the official laboratory protocols for measuring this efficacy are important considerations for understanding the relevance of antimicrobial agents and compositions. Antimicrobial compositions may effect two kinds of microbial cell damage. The first is a truly lethal, irreversible action resulting in complete microbial cell destruction or incapacitation. The second type of cell damage is reversible, such that if the organism is rendered free or the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

BRIEF DESCRIPTION OF THE FIGURES

FIG. 5 is a graphical depiction of certain results obtained from Working Example 7.

DETAILED DESCRIPTION OF THE INVENTION

Figure 1:
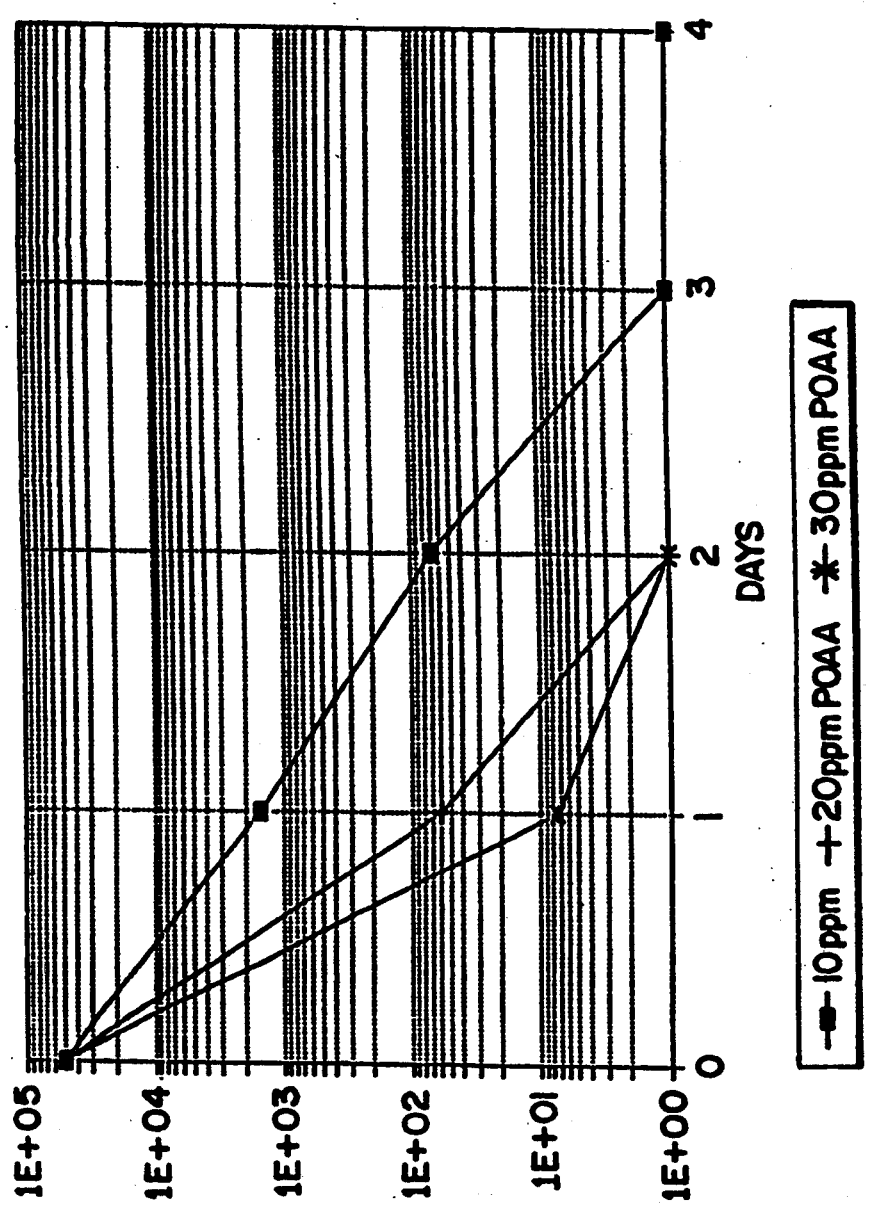
FIG. 1 is a graphical depiction of the results of Working Example 4.

A process for preventing microbial growth in aqueous streams, said process comprising the step of applying an effective antimicrobial concentration of a percarboxylic acid composition, to the aqueous stream.

Carboxylic Acid

Among other constituents, the invention comprises a carboxylic acid. Generally, carboxylic acids have the formula R-COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three, or more carboxyl groups.

Carboxylic acids have a tendency to acidify aqueous compositions in which they are present as the hydrogen atom of the carboxyl group is active and may appear as an anion. The carboxylic acid constituent within the present composition when combined with aqueous hydrogen peroxide generally functions as an antimicrobial agent as a result of the presence of the active hydrogen atom. Moreover, the carboxylic acid constituent within the invention maintains the composition at an acidic pH.

Carboxylic acids which are generally useful in the process of the invention are those which comprise percarboxylic acids. Percarboxylic acids generally have the formula $R(CO_3H)_N$, where R is an alkyl, arylalkyl, cycloalkyl, aromatic or heterocyclic group, and N is one or two, or named by prefixing the parent acid with peroxy.

While peroxy carboxylic acids are not very stable, their stability generally increases with increasing molecular weight. Thermal decomposition of these acids may generally proceed by free radical and nonradical paths, by photodecomposition or radical-induced decomposition, or by the action of metal ions or complexes. Percarboxylic acids may be made by the direct, acid catalyzed equilibrium action of 30-98 wt. % hydrogen peroxide with the carboxylic acid, by autoxidation of aldehydes, or from acid chlorides, and hydrides, or carboxylic anhydrides with hydrogen or sodium peroxide.

Percarboxylic acids useful in this invention include peracetic acid, peroctanoic acid, perglutaric acid, persuccinic acid, perdecanoic acid or mixtures thereof. These percarboxylic acids have been found to provide good antimicrobial action with good stability in aqueous streams.

Preferably, the process of the invention uses a combination of peracetic acid and peroctanoic acid. This combination of percarboxylic acids has been found to provide preferred antimicrobial efficacy and stability in the presence of high organic loads. Generally, within the sanitizer, the concentration of peroctanoic acid may range from about 10 wt % to 90 wt % and preferably from about 10 wt % to 20 wt %. The concentration of peracetic acid may range from about 10 wt % to 90 wt % and preferably from about 80 wt % to 90 wt %.

In its most preferred mode, the process of the invention uses peracetic acid. Peracetic acid is a peroxy carboxylic acid having the formula:

Generally, peracetic acid is a liquid having an acrid odor and is freely soluble in water, alcohol, ether, and sulfuric acid. Peracetic acid may be prepared through any number of means known to those of skill in the art including preparation from acetaldehyde and oxygen in the presence of cobalt acetate. A 50% solution of peracetic acid may be obtained by combining acetic anhydride, hydrogen peroxide and sulfuric acid. Other methods of formulation of peracetic acid include those disclosed in U.S. Pat. No. 2,833,813, which is incorporated herein by reference.

Hydrogen Peroxide

The antimicrobial composition of the invention may also comprise a hydrogen peroxide constituent. Hydrogen peroxide in combination with the percarboxylic acid provides a surprising level of antimicrobial action against microorganisms despite the presence of high loadings of organic sediment. Additionally, hydrogen peroxide may provide an effervescent action which may irrigate any surface to which it is applied. Hydrogen peroxide works with a mechanical flushing action once applied which further cleans the surface of application. An additional advantage of hydrogen peroxide is the food compatibility of this composition upon use and decomposition. For example, combinations of peracetic acid and hydrogen peroxide result in acetic acid, water, and oxygen upon decomposition all of which are food product compatible.

While many oxidizing agents may be used, hydrogen peroxide is generally preferred for a number of reasons. After application of the $H_2O_2$/peracetic acid germicidal agent, the residue left merely comprises water and an acidic constituent. Deposition of these products on the surface of application such as a flume, will not adversely effect the process or the food products transported therein.

Hydrogen peroxide ($H_2O_2$), has a molecular weight of 34.014 and it is a weakly acidic, clear, colorless liquid. The four atoms are covalently bonded in a non-polar H—O—O—H structure. Generally, hydrogen peroxide has a melting point of $-0.41°$ C., a boiling point of $150.2°$ C., a density at $25°$ C. of 1.4425 grams per cm$^3$, and a viscosity of 1.245 centipoise at $20°$ C.

Generally, the concentration of hydrogen peroxide within the composition used in the process of the invention ranges from about 1 weight percent to about 50 weight percent, preferably from about 3 weight percent to about 40 weight percent, and most preferably from about 5 weight percent to about 30 weight percent. This concentration of hydrogen peroxide is most preferred as providing an optimal antimicrobial effect.

These concentrations of hydrogen peroxide may be increased or decreased while still remaining within the scope of the invention.

Adjuvants

The antimicrobial composition of the invention may also comprise any number of adjuvants. Specifically, the composition of the invention may comprise stabilizing agents, wetting agents, as well as pigments or dyes among any number of constituents which may be added to the composition.

Stabilizing agents may be added to the composition of the invention to stabilize the peracid and hydrogen peroxide and prevent the premature oxidation of this constituent within the composition of the invention. Chelating agents or sequestrants generally useful if stabilizing agents in the invention include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethylidene-1, 1-diphosphonic acid ($CH_3C(PO_3H_2)_2OH$), amino[tri(methylene phosphonic acid)] ([$CH_2PO_3H_2$]$_2$(ethylene diamine[tetra methylene-phosphonic acid)], 2-phosphene butane-1, 2, 4-tricarboxylic acid, as well as the alkyl metal salts, ammonium salts, or alkanol amine salts, such as mono, di, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Also useful in the composition of the invention are wetting and defoaming agents. Wetting agents function to increase the penetration activity of the antimicrobial composition of the invention. Wetting agents which may be used in the composition of the invention include any of those constituents known within the art to raise the surface activity of the composition of the invention.

Along these lines surfactants, and especially nonionic surfactants, may also be useful in the present invention. Nonionic surfactants which may be useful in the present invention are those which comprise ethylene oxide moieties, propylene oxide moieties, as well a mixtures thereof, and ethylene oxide-propylene oxide moieties in either heteric or block formation. Additionally useful in the present invention are nonionic surfactants which comprise an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to an alkyl chain where the ethylene oxide and propylene oxide moieties may be in any randomized or ordered pattern and of any specific length. Nonionic surfactants useful in the present invention may also comprise randomized sections of block and heteric ethylene oxide propylene oxide, or ethylene oxide-propylene oxide.

Generally, the concentration of nonionic surfactant used in the invention may range from about 0 wt % to about 5 wt % of the composition, preferably from about 0 wt % to about 2 wt % of the concentrate composition, and most preferably from about 0 wt % to about 1 wt % of the composition.

The composition used in the process of the invention may also contain additional ingredients as necessary to assist in defoaming.

Generally, defoamers which may be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferable, are those antifoaming agents or defoamers which are of food grade quality given the application of the process of the invention. To this end, one of the more effective antifoaming agents comprises silicones. Silicones such as dimethyl silicone, glycol polysiloxane, methylphenol polysiloxane, trialkyl or tetralkyl silanes, hydrophobic silica defoamers and mixtures thereof may all be used in defoaming applications. Commercial defoamers commonly available include silicones such as Ardefoam ® from Armour Industrial Chemical Company which is a silicone bound in an organic emulsion; Foam Kill ® or Kresseo ® available from Krusable Chemical Company which are silicone and non-silicone type defoamers as well as silicone esters; and Anti-Foam A® and DC-200 TM from Dow Corning Corporation which are both food grade type silicones among others. These defoamers are generally present at a concentration range from about 0 wt % to 5 wt %, preferably from about 0 wt % to 2 wt %, and most preferably from about 0 wt % to about 1 wt %.

The invention may also contain any number of other constituents as necessitated by the application, which are known to those of skill in the art and which may facilitate the activity of the present invention.

The composition used in the invention may comprise:

|  | Composition (Wt %) | | |
| --- | --- | --- | --- |
|  | Useful | Working | Preferred |
| Percarboxylic Acid | 2–25 | 2–20 | 4–20 |
| $H_2O_2$ | 1–45 | 5–35 | 7–30 |
| Acetic Acid | 1–70 | 3–55 | 5–45 |
| Water | Balance | Balance | Balance |

|  | Initial Concentration in Transport Water | | |
| --- | --- | --- | --- |
| Constituent | Useful | Working | Preferred |
| Percarboxylic Acid | 5–100 ppm | 5–60 ppm | 10–50 ppm |
| $H_2O_2$ | 5–500 ppm | 5–300 ppm | 5–250 ppm |

Once the antimicrobial of the invention is applied to any given transport stream, the antimicrobial will be subjected to a demand resulting from microbes present in the stream as well as other organic or inorganic material present in the stream. As a general guideline, not limiting of the invention, the following concentrations of antimicrobial may be found after demand.

|  | Residual Concentration (ppm) After Demand | | |
| --- | --- | --- | --- |
| Constituent | Useful | Working | Preferred |
| Percarboxylic Acid | 1–85 | 1–45 | 1–35 |
| $H_2O_2$ | 1–490 | 1–290 | 1–240 |

While the demand may reduce the antimicrobial concentration to zero, at least about 1 ppm of POAA is generally preferred to provide the intended efficacy.

Generation of Peroxy Acids

The process of the invention may also be initiated through the use of peroxy acid concentrate compositions. In such a case, the percarboxylic acid may either be generated naturally or through the combination of a hydrogen peroxide concentrate together with a carboxylic acid concentrate at the sight of use such as that process which is disclosed in Lokkesmoe et al, U.S. Pat. No. 5,122,538, issued Jun. 16, 1992, which is incorporated herein by reference. In such a case, the composition may be formed from a hydrogen peroxide concentrate comprising varying levels of hydrogen peroxide and stabilizer as shown in the table below.

|  | Concentration (Wt %) | | |
| --- | --- | --- | --- |
| Constituent | Useful | Working | Preferred |
| Hydrogen Peroxide | 5–70 | 15–70 | 25–60 |
| Stabilizer | 0–10 | 0–5 | 0.1–3 |
| $H_2O$ | 20–95 | 25–85 | 37–75 |

When combined with a carboxylic acid, the two concentrates result in a peroxy carboxylic acid. Generally, the carboxylic acid concentrate comprises a carboxylic acid in water as shown in the table-found below.

|  | Concentration (Wt %) | | |
| --- | --- | --- | --- |
| Constituent | Useful | Working | Preferred |
| Carboxylic Acid | 50–100 | 65–100 | 80–100 |
| Water | 0–50 | 0–35 | 0–20 |

Working Examples

The invention will now be described in more detail by reference to the following examples. The only proper construction of these examples is as non-limiting illustrative examples showing various formulations, stabilities, and applications of the invention.

Working Example 1

To prepare stock solution of concentrate peracetic acid (or "POAA") formula for use in the flume experiments, the following components were combined.

| Component | Wt % |
| --- | --- |
| Acetic Acid | 43.85 |
| Hydrogen Peroxide 35% | 50.85 |
| Dequest 2010 (60% active) 1-Hydroxyethylidene-1,1-Diphosphonic Acid | 1.5 |
| $H_2O$ | 3.8 |

The result of this combination was a composition having the following constituency.

|  | Wt % |
| --- | --- |
| Acetic Acid | 32.0 |
| $H_2O_2$ | 11.1 |
| Dequest 2010 | 0.90 |
| $H_2O$ | 41.0 |
| Peracetic Acid | 15.0 |

Working Example 2

In the second working example, the immediate demand of 1% and 3% tomato solutions for POAA was determined. POAA in pure water (control) was compared with similar dilutions in 1% and 3% tomato solutions.

TABLE 1

|  | Control (no tomatoes) | 1% Tomato | 3% Tomato |
| --- | --- | --- | --- |
| Mean POAA conc. (ppm) | 111.8 | 112.25 | 111.0 |
| Mean $H_2O_2$ conc. (ppm) | 65.2 | 65.3 | 64.7 |
| Number of Trials | 3 | 2 | 1 |
| Std Dev. (POAA) | 0.61 | 0.21 | — |

TABLE 1-continued

|  | Control (no tomatoes) | 1% Tomato | 3% Tomato |
|---|---|---|---|
| Std Dev. (H$_2$O$_2$) | 0.10 | 0.14 | — |

No initial decrease in the POAA concentration was seen.

Working Example 3

The third working example expanded the time frame of testing to 8 days for 20 ppm POAA solutions made from both 5% and 15% POAA formulations. Again, 1% tomato solutions were used. Tables 2–5 show that 93% to 100% of the POAA remains initially. After four days, 32% to 61% POAA was left after contacting a 1% tomato solution for the 5% and 15% POAA formulas, respectively. Tables 4 and 5 represent hydrogen peroxide control solutions compared under the same analytical protocol.

TABLE 2

| | (5% POAA) | | | |
|---|---|---|---|---|
| | CONTROL | | 1% TOMATO | |
| DAY | POAA PPM | % REMAIN | POAA PPM | % REMAIN |
| 0 | 17.66 | 100% | 16.47 | 100% |
| 1 | 19.66 | 111% | 13.23 | 80% |
| 2 | 16.04 | 91% | 10.23 | 62% |
| 3 | 16.04 | 91% | 7.22 | 44% |
| 4 | — | — | 5.24 | 32% |
| 5 | — | — | — | — |
| 6 | — | — | — | — |
| 7 | 13.38 | 76% | — | — |
| 8 | 12.77 | 72% | — | — |
| | pH = 4.01 | | pH = 4.60 | |

INITIAL PERCENTAGE OF CONTROL = 93%

TABLE 3

| | (15% POAA) | | | |
|---|---|---|---|---|
| | CONTROL | | 1% TOMATO | |
| DAY | POAA PPM | % REMAIN | POAA PPM | % REMAIN |
| 0 | 17.19 | 100% | 18.87 | 100% |
| 1 | 17.04 | 99% | 15.86 | 84% |
| 2 | 15.20 | 88% | 14.71 | 78% |
| 3 | 13.76 | 80% | 13.00 | 69% |
| 4 | — | — | 11.55 | 61% |
| 5 | — | — | — | — |
| 6 | — | — | — | — |
| 7 | 7.90 | 46% | — | — |
| 8 | 6.99 | 41% | 7.30 | 39% |
| | pH = 3.92 | | pH = 4.13 | |

INITIAL PERCENTAGE OF CONTROL = 110%

TABLE 4

| | (5% POAA) | | | |
|---|---|---|---|---|
| | CONTROL | | 1% TOMATO | |
| DAY | H202 PPM | % REMAIN | H202 PPM | % REMAIN |
| 0 | 83.45 | 100% | 82.27 | 100% |
| 1 | 84.69 | 101% | 81.54 | 99% |
| 2 | 83.77 | 100% | 80.89 | 98% |
| 3 | 84.32 | 101% | 79.53 | 97% |
| 4 | — | — | 75.85 | 92% |
| 5 | — | — | — | — |
| 6 | — | — | — | — |
| 7 | 84.35 | 101% | — | — |
| 8 | 84.66 | 101% | — | — |

TABLE 4-continued

| | (5% POAA) | | | |
|---|---|---|---|---|
| | CONTROL | | 1% TOMATO | |
| DAY | H202 PPM | % REMAIN | H202 PPM | % REMAIN |
| | pH = 4.01 | | pH = 4.60 | |

INITIAL PERCENTAGE OF CONTROL = 99%

TABLE 5

| | (15% POAA) | | | |
|---|---|---|---|---|
| | CONTROL | | 1% TOMATO | |
| DAY | H202 PPM | % REMAIN | H202 PPM | % REMAIN |
| 0 | 10.27 | 100% | 10.89 | 100% |
| 1 | 10.99 | 107% | 10.40 | 96% |
| 2 | 11.15 | 109% | 10.64 | 98% |
| 3 | 11.15 | 109% | 10.23 | 94% |
| 4 | — | — | 10.00 | 92% |
| 5 | — | — | — | — |
| 6 | — | — | — | — |
| 7 | 10.18 | 99% | — | — |
| 8 | 10.57 | 103% | 8.06 | 74% |
| | pH = 3.92 | | pH = 4.13 | |

INITIAL PERCENTAGE OF CONTROL = 106%

Working Example 4

The fourth working example provided a set of stability experiments expanded to the use of peas, beans, and corn. Tables 6–13 show the stability of a formula which is mostly peracetic acid (with peroctanoic acid being approximately 10 wt % of the total peracetic and peroctanoic acid content) in 1% solutions of these vegetables. The initial concentrations were 70%, 100% and 90% of the control solutions (with no vegetable) for corn, beans, and peas, respectively. After 3 days, 31%, 47% and 32%, respectively, of the initial concentration of peracids such as POAA was left for these vegetables. The peracids showed surprising stability in solutions comprising a high concentration of organic material.

TABLE 6

| | (CONTROL) | |
|---|---|---|
| DAY | TOTAL PERACIDS (AS POAA) PPM | % REMAIN |
| 0 | 18.85 | 100% |
| 1 | 19.76 | 100% |
| 2 | 18.77 | 100% |
| 3 | 16.80 | 89% |

TABLE 7

| | (1% CORN) | |
|---|---|---|
| DAY | TOTAL PERACIDS (AS POAA) PPM | % REMAIN |
| 0 | 13.15 | 100% |
| 1 | 8.51 | 65% |
| 2 | 6.16 | 47% |
| 3 | 4.03 | 31% |

INITIAL PERCENTAGE OF CONTROL = 70%

TABLE 8

| | (1% BEANS) | |
|---|---|---|
| DAY | TOTAL PERACIDS (AS POAA) PPM | % REMAIN |
| 0 | 21.36 | 100% |
| 1 | 17.48 | 82% |
| 2 | 14.36 | 67% |
| 3 | 9.96 | 47% |

INITIAL PERCENTAGE OF CONTROL = 113%

TABLE 9

| | (1% PEAS) | |
|---|---|---|
| DAY | TOTAL PERACIDS (AS POAA) PPM | % REMAIN |
| 0 | 18.09 | 100% |
| 1 | 12.46 | 69% |
| 2 | 10.41 | 58% |
| 3 | 5.70 | 32% |

INITIAL PERCENTAGE OF CONTROL = 96%

TABLE 10

| | (CONTROL) | |
|---|---|---|
| DAY | H2O2 PPM | % REMAIN |
| 0 | 10.30 | 100% |
| 1 | 10.98 | 107% |
| 2 | 10.91 | 106% |
| 3 | 10.85 | 105% |

TABLE 11

| | (1% CORN) | |
|---|---|---|
| DAY | H2O2 PPM | % REMAIN |
| 0 | 15.67 | 100% |
| 1 | 7.21 | 46% |
| 2 | 5.71 | 36% |
| 3 | 1.70 | 11% |

INITIAL PERCENTAGE OF CONTROL = 152%

TABLE 12

| | (1% BEANS) | |
|---|---|---|
| DAY | H2O2 PPM | % REMAIN |
| 0 | 8.84 | 100% |
| 1 | 3.09 | 35% |
| 2 | 1.63 | 18% |
| 3 | 1.09 | 12% |

INITIAL PERCENTAGE OF CONTROL = 86%

TABLE 13

| | (1% PEAS) | |
|---|---|---|
| DAY | H2O2 PPM | % REMAIN |
| 0 | 8.57 | 100% |
| 1 | 4.83 | 56% |
| 2 | 3.37 | 39% |
| 3 | 0.78 | 9% |

INITIAL PERCENTAGE OF CONTROL = 83%

Working Example 5

Experiments testing the efficacy of POAA on molds and bacteria showed no microbial growth at concentrations of 5, 10 and 20 ppm POAA in 1% peas solution. As can be seen in FIG. 1, later experiments show good control of molds with 10-30 ppm POAA in 1% peas solution.

Figure 2:
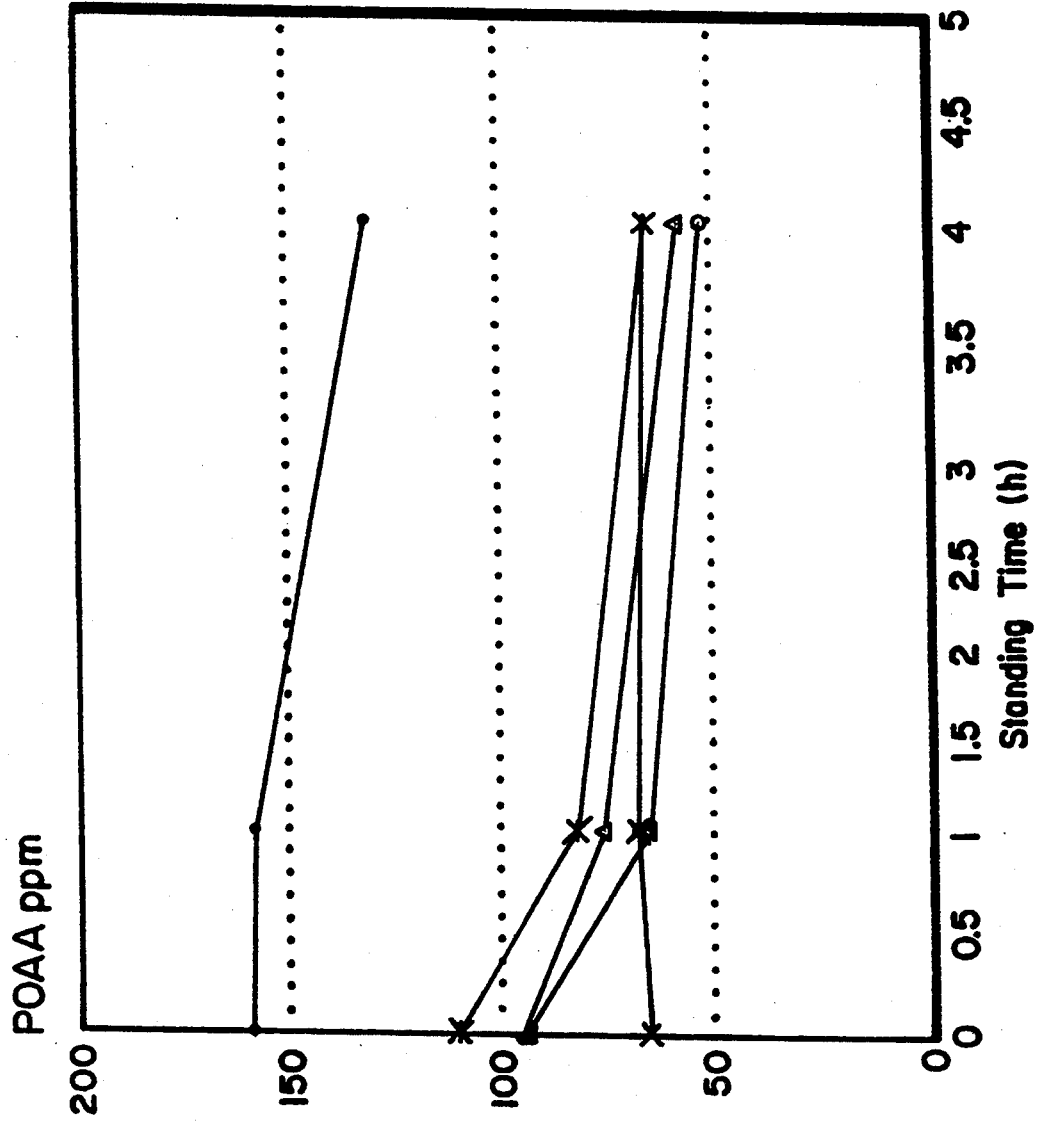
FIGS. 2 and 3 are graphical depictions of the results of Working Example 5.
Figure 3:
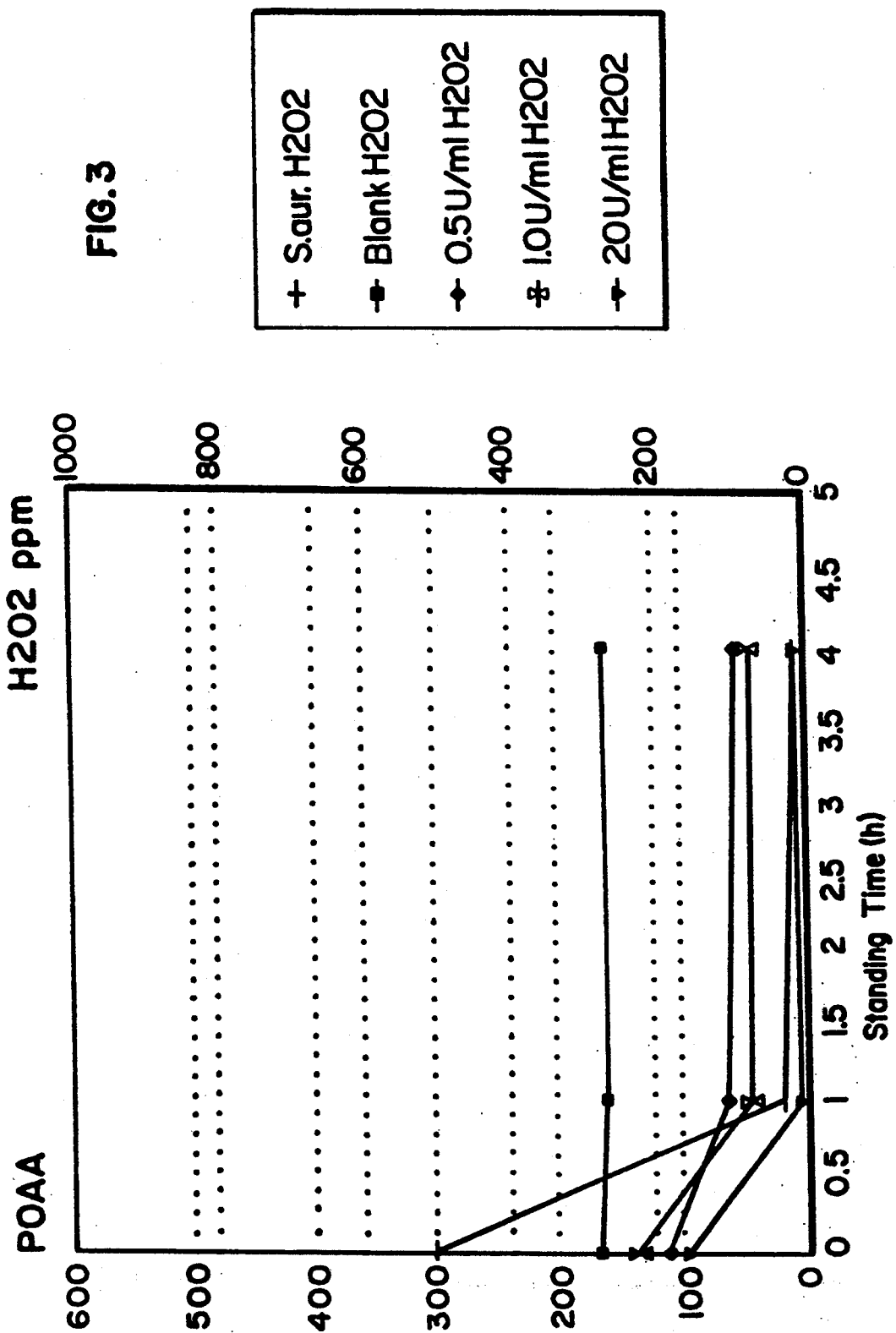

Working Example 6 An experiment was completed to obtain a better understanding of the effect of catalase on POAA/$H_2O_2$ solutions. In this experiment, POAA and $H_2O_2$ were added to solutions containing a variety of concentration of catalase and in one a 1:50 dilution of an overnight culture of S. aureus. POAA and $H_2O_2$ concentrations were then monitored in the presence of catalase by titration along with the catalase activity in each solution. The results of this experiment are shown in Table 14 and in FIGS. 2 and 3.

TABLE 14

POAA Stability in the Presence of Catalase (CTS)

| Sample | *Catalase Activity | Initial ppm POAA | Initial ppm $H_2O_2$ |
|---|---|---|---|
| Blank (PO4) | 0 | 100 | 277 |
| S.aureus | 2.8 | 158 | 505 |
| 0.5 U/ml | 0.34 | 65 | 185 |
| 1.0 U/ml | 0.66 | 95 | 225 |
| 20 U/ml | 20 | 95 | 155 |

| Sample | *Catalase Activity | 1 Hour ppm POAA | 1 Hour ppm $H_2O_2$ |
|---|---|---|---|
| Blank (PO4) | 0 | 82 | 268 |
| S.aureus | 1.1 | 158 | 27 |
| 0.5 U/ml | ND** | 68 | 102 |
| 1.0 U/ml | ND | 76 | 71 |
| 20 U/ml | 10 | 65 | 4 |

| Sample | *Catalase Activity | 4 Hours ppm POAA | 4 Hours ppm $H_2O_2$ |
|---|---|---|---|
| Blank (PO4) | 0 | 65 | 267 |
| S.aureus | 0.08 | 131 | 8 |
| 0.5 U/ml | ND | 65 | 82 |
| 1.0 U/ml | ND | 57 | 66 |
| 20 U/ml | .21 | 52 | 7 |

*Activity is expressed as micromoles of $H_2O_2$ hydrolyzed in 1 minute.
**Not Detected The test was done at room temperature and the concentrations of catalase used were lower than those seen in a culture. The presence of the catalase did accelerate the decomposition of $H_2O_2$ but did not accelerate the decomposition of the POAA at these concentrations.

Working Example 7

Figure 4:
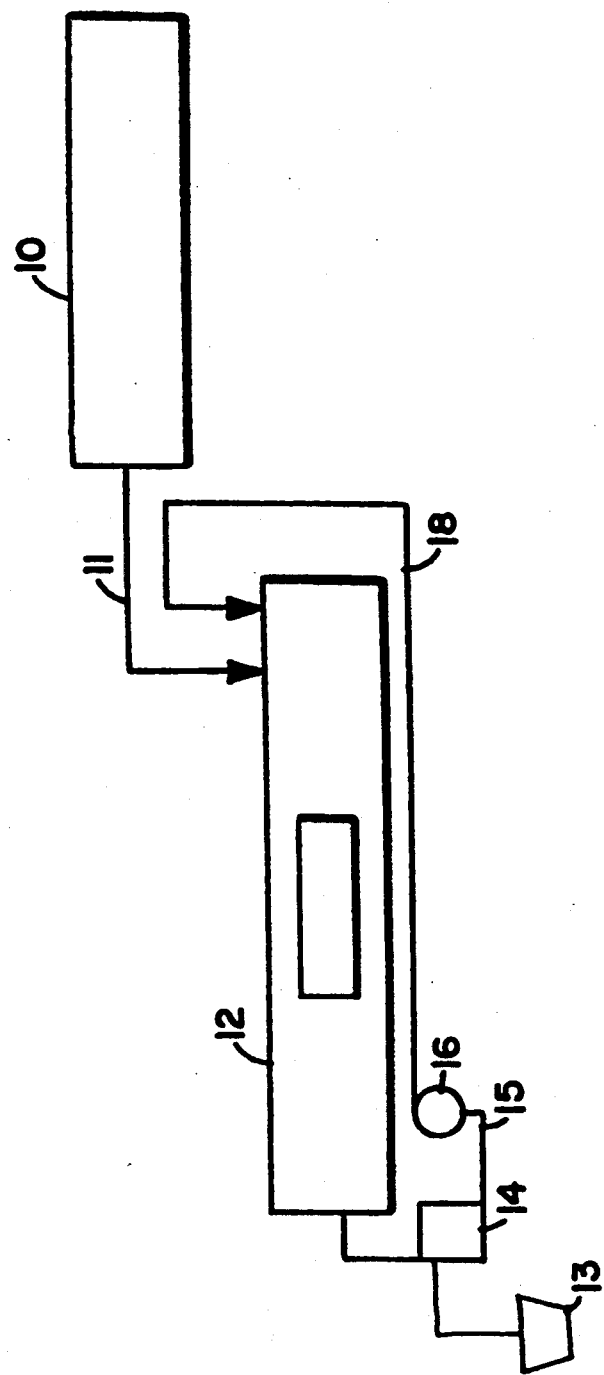
FIG. 4 is a schematic depiction of a flume system used in conjunction with Working Example 7.

An analysis of the invention was then undertaken in the context of an actual flume delivery system. As can be seen in FIG. 4, a flume system comprising a make-up tank 10, a flow line 11, a flume tank 12, an overflow tank 14 with discharge pipe or drain 13, pumpline 15, pump 16, and recycle line 18 were assembled to model the conditions in food transport flumes used in food processing plants. The make-up water comprised 16 grains/gal of $CaCO_3$ and was introduced into the flume at a rate of 343 ml/min. A pea solution was introduced into the make-up tank 10 comprising 10% ground peas in hard water. The pea solution was diluted to 1% in the flume through a flow rate of 42.5 ml/min. Also added to the make-up water was a dirt solution comprising 3.6% top soil which was diluted to 0.3% in the flume by a flow rate of 35 ml/min. Lastly, a sanitizer was added to the flume assembly and diluted by a factor of 100 through a flow rate of 42 ml/min. The initial concentration and formulation for the sanitizers analyzed can be seen in Table 15 below.

TABLE 15

| Working Example | Active/ Concentration | Condition |
|---|---|---|
| 7A | 30 ppm POAA | Sterile peas |

TABLE 15-continued

| Working Example | Active/ Concentration | Condition |
|---|---|---|
| Control 1 | — | Sterile peas |
| 7B | NaOCl/110 ppm Cl | — |
| 7C | NaOCl/30 ppm Cl | — |
| 7D | 30 ppm POAA | Pulsed feed |
| 7E | 40 ppm POAA | Continuous feed |
| 7F | 3 ppm POOA*/ 27 ppm POAA | — |
| Control 2 | — | — |
| 7G | 20 PPM ClO$_2$ | 3.7 ml/min flow rate |
| 7H | 1.5 ppm POOA*/ 13.5 POAA | — |

*POOA is Peroctanoic Acid

The total flow rate in the flume was 425 ml/min with a recycle flow rate created by pump 16 of 3 gallons/min. The total flume volume was 2.25 gallons with overflow discharged out of overflow tank 14 into discharge reservoir 13. Analysis for metals present in the water exiting the flume from a previous experiment gave an average of 13.4 ppm iron (Fe), 0.28 ppm copper (Cu), and 0.52 ppm manganese (Mn).

The results of the analysis can be seen in Table 16 and FIG. 5.

TABLE 16

| Working Example | Avg. Residual (ppm) | Avg. Demand (ppm) | Avg. pH | Avg. Flume cts. | Avg. Log Red. vs Control | Avg. Pea cts. |
|---|---|---|---|---|---|---|
| 7A | 14.9 | 15.1 | 7.5 | 1.7E + 03 | 2.8 | 5.0E + 04 |
| Control 1 | — | — | NA | 1.0E + 06 | — | 3.9E + 04 |
| 7B | 41 | 69 | 8.4 | 2.2E + 04 | 2.0 | 1.2E + 06 |
| 7C | 19 | 11 | 8.2 | 4.9E + 04 | 1.7 | 1.2E + 06 |
| 7D | 15.7 | 14.3 | 7.53 | 9.5E + 03 | 2.4 | 2.0E + 06 |
| 7E | 24.1 | 15.9 | 7.4 | 1.5E + 04 | 2.2 | 7.1E + 04 |
| 7F | 20 | 10 | 6.3 | 9.5E + 03 | 2.4 | 2.3E + 04 |
| Control 2 | — | — | NA | 2.2E + 06 | — | 1.4E + 05 |
| 7G | 0 | 17.5 | NA | 1.4E + 04 | 2.2 | 1.7E + 05 |
| 7H | 5 | 10 | 7.2 | 4.0E + 04 | 1.7 | 5.0E + 05 |

The above discussion, examples, and data illustrate our current understanding of the invention. However, since many variations of the invention can be made without departing from the spirit and scope of the invention, the invention resides wholly in the claims hereinafter appended.

We claim:

1. A method of controlling microbial growth in an aqueous stream used for transporting food products comprising the step of treating said aqueous stream with
   (i) from about 5 to 100 ppm of a percarboxylic acid selected from the group consisting of peracetic, peroctanoic, perdecanoic, and mixtures thereof; and
   (ii) from about 5 ppm to 500 ppm of hydrogen peroxide.

2. The method of claim 1 wherein said percarboxylic acid is peracetic acid.

3. The method of claim 1 wherein said percarboxylic acid is selected from the group consisting of peracetic acid, peroctanoic acid, and mixtures thereof present in a total concentration ranging from about 5 ppm to 100 ppm.

4. A method of controlling microbial growth in an aqueous stream used for transporting food products by administering an antimicrobial composition to said stream, said antimicrobial composition comprising:
   (i) from about 5 to 100 ppm of a percarboxylic acid selected from the group consisting of peracetic, peroctanoic, perdecanoic, and mixtures thereof initially in the aqueous stream; and
   (ii) from about 5 to 500 ppm hydrogen peroxide initially in the aqueous stream,
   said method comprising the steps of
   (a) forming said antimicrobial composition by combining a first concentrate comprising hydrogen peroxide and a second concentrate selected from the group consisting of acetic, octanoic, decanoic, and mixtures thereof; and
   (b) administering said antimicrobial composition to said aqueous stream used for transporting products.

5. The method of claim 4 wherein said percarboxylic acid is peracetic acid.

6. The method of claim 4 wherein said percarboxylic acid is selected from the group consisting of peracetic acid, peroctanoic acid, and mixtures thereof present in an initial concentration ranging from about 5 ppm to 100 ppm.

7. The method of claim 4 wherein said antimicrobial composition comprises a wetting agent present in a concentration ranging from about 0 to 1 wt %.

8. A method of controlling microbial growth in an aqueous stream used for transporting food products, said method comprising the step of treating said aqueous stream with an antimicrobial composition, said antimicrobial composition comprising:
   (a) from about 5 to 100 ppm peracetic acid initially in the aqueous stream; and
   (b) from about 5 to 500 ppm hydrogen peroxide initially in the aqueous stream.

9. The method of claim 8 wherein said antimicrobial composition further comprises a nonionic surfactant.

10. The method of claim 8 wherein said peracetic acid is present in a concentration ranging from about 5 to 60 ppm in the aqueous stream.

11. The method of claim 8 wherein said hydrogen peroxide is present in a concentration ranging from about 5 to 300 ppm.

12. A method of controlling microbial growth in an aqueous stream used for transporting food products, said method comprising the steps of:
   (a) forming an antimicrobial composition by combining a first concentrate comprising from about 5 wt % to 70 wt % H$_2$O$_2$ with a second concentrate comprising from about 50 wt % to 100 wt % of a carboxylic acid selected from the group consisting of acetic, octanoic, decanoic and mixtures thereof;
   (b) forming a corresponding percarboxylic acid within said antimicrobial composition; and
   (c) treating the aqueous stream with said antimicrobial composition, wherein said hydrogen peroxide is present in an initial concentration ranging from about 5 ppm to 500 ppm and said percarboxylic acid is present in an initial concentration ranging from about 5 ppm to 100 ppm in the aqueous food delivery stream.

13. The method of claim 12 wherein said percarboxylic acid is peracetic acid.

14. The method of claim 12 wherein said percarboxylic acid is selected from the group consisting of peracetic acid, peroctanoic acid, and mixtures thereof present in a total concentration ranging from about 5 ppm to 100 ppm.

* * * * *

UNITED STATES PATENT AND TRADEMARK OFFICE
CERTIFICATE OF CORRECTION

PATENT NO.  :  5,409,713

DATED        :  April 25, 1995

INVENTOR(S) :  Keith Lokkesmoe, et al.

It is certified that error appears in the above-identified patent and that said Letters Patent is hereby corrected as shown below:

Column 3, line 46 "or" should read --of--

Column 6, line 23 "a" should read --as--

Column 7, line 6 "DC-200 TM" should read --DC200™--

Column 12, line 1 "Working Example 6" should be on line 1 as a heading

Signed and Sealed this

Twenty-first Day of November, 1995

*Attest:*

BRUCE LEHMAN

*Attesting Officer*     *Commissioner of Patents and Trademarks*